US006379686B1

(12) United States Patent
Harris et al.

(10) Patent No.: US 6,379,686 B1
(45) Date of Patent: Apr. 30, 2002

(54) FABRIC, CARPET AND UPHOLSTERY PROTECTANT WITH BIOCIDE AND ACARICIDE

(75) Inventors: James T. Harris; Bernardus M. Tangelder, both of London (CA)

(73) Assignee: MagiSeal Corporation, London (CA)

( * ) Notice: Subject to any disclaimer, the term of this patent is extended or adjusted under 35 U.S.C. 154(b) by 0 days.

(21) Appl. No.: 09/228,737

(22) Filed: Jan. 12, 1999

Related U.S. Application Data

(60) Provisional application No. 60/093,221, filed on Jul. 17, 1998.

(51) Int. Cl.⁷ .................... A61K 31/74; A01N 25/00
(52) U.S. Cl. .................. 424/405; 424/409; 424/410; 424/78.02; 424/78.05; 514/65; 514/67; 514/70; 43/132.1; 43/136
(58) Field of Search .................. 424/405, 409, 424/410, 78.02, 78.05; 514/65, 67, 70; 43/132.1, 136

(56) References Cited

U.S. PATENT DOCUMENTS

| | | | |
|---|---|---|---|
| 3,068,187 A | * 12/1962 | Bostad et al. | |
| 4,100,225 A | * 7/1978 | Mueller | 260/878 R |
| 4,502,861 A | * 3/1985 | Becker et al. | 8/490 |
| 4,666,940 A | 5/1987 | Bischoff et al. | 514/544 |
| 4,777,180 A | * 10/1988 | Tessier et al. | 514/389 |
| 4,806,526 A | 2/1989 | Green | 514/23 |
| 5,126,138 A | 6/1992 | McGee et al. | 424/404 |
| 5,149,365 A | * 9/1992 | Landsiedel et al. | 106/18.32 |
| 5,178,872 A | 1/1993 | Ohtsubo et al. | 424/408 |
| 5,180,586 A | 1/1993 | Sato et al. | 424/405 |
| 5,198,287 A | 3/1993 | Samson et al. | 428/248 |
| 5,252,387 A | 10/1993 | Samson et al. | 428/248 |
| 5,326,777 A | 7/1994 | Ludwig et al. | 514/383 |
| 5,346,704 A | 9/1994 | Lajoie | 424/717 |
| 5,350,795 A | 9/1994 | Smith et al. | 524/507 |
| 5,385,926 A | 1/1995 | Ludwig et al. | 514/383 |
| 5,407,920 A | * 4/1995 | Dawson | 514/65 |
| 5,417,977 A | 5/1995 | Honeycutt | 424/443 |
| 5,453,275 A | 9/1995 | Terry et al. | 424/405 |
| 5,527,582 A | 6/1996 | Callebert | 428/95 |
| 5,547,679 A | 8/1996 | Ueda et al. | 424/402 |
| 5,622,546 A | 4/1997 | Elbe et al. | 106/18.33 |
| 5,635,192 A | 6/1997 | Terry et al. | 424/405 |
| 5,639,464 A | 6/1997 | Terry et al. | 424/405 |
| 5,712,275 A | 1/1998 | Van Gestel | 514/222.5 |
| 5,719,114 A | * 2/1998 | Zocchi et al. | 510/383 |
| 5,725,789 A | 3/1998 | Huber et al. | 252/8.62 |
| 5,756,113 A | * 5/1998 | Kelley | 424/405 |
| 5,792,465 A | 8/1998 | Hagarty | 424/405 |
| 5,804,591 A | 9/1998 | Valcke et al. | 514/383 |
| 5,843,981 A | * 12/1998 | Miller | 514/421 |
| 5,916,580 A | 6/1999 | Shober et al. | |
| 5,916,917 A | * 6/1999 | Suh et al. | 514/544 |
| 5,919,751 A | 7/1999 | Bird et al. | |

FOREIGN PATENT DOCUMENTS

| | | |
|---|---|---|
| DE | 29622338 | 3/1997 |
| WO | WO 92/16103 | 10/1992 |
| WO | PCT/BE96/00135 | 12/1996 |
| WO | WO 97/24484 | 7/1997 |

OTHER PUBLICATIONS

Database WPI, Derwent Publications Ltd., London, GB; AN 1997–209183 XP0021232354 Kao Corporation: "Household insecticidal compsn.–contains quaternary ammonium salt, and insecticide e.g. pyrethroid" abstract & JP 09 059109 A.

Database WPI, Derwent Publications Ltd., London, GB; AN 1986–116639 XP002123255 Sanyo Mokuzai Bofu KK: "Insecticidal and ant controlling compsn. contg. phosphate and/or quat. pyrethroid insecticide and amine cpd. and/or ammonium cpd." abstract & JP 61 057506 A.

* cited by examiner

*Primary Examiner*—Frederick Krass
(74) *Attorney, Agent, or Firm*—Pearne & Gordon LLP

(57) ABSTRACT

A composition for treating a substrate to control dust mite populations thereon. The composition includes a fluoropolymer, a biocide, and an acaricide.

31 Claims, No Drawings

FABRIC, CARPET AND UPHOLSTERY PROTECTANT WITH BIOCIDE AND ACARICIDE

CROSS-REFERENCE TO RELATED APPLICATION

This application claims the benefits of U.S. Provisional Application No. 60/093,221, filed Jul. 17, 1998.

BACKGROUND OF THE INVENTION

This invention relates to compositions for treating substrates, and in particular to compositions for treating substrates to control dust mites.

Allergies to dust are common in the U.S. and Western European countries. Many of these allergies are caused by allergens produced by acarids present in dust, such as *Dermatophagoides farinae, Euroglyphus maynei*, and *Dermatophagoides pteronyssinus*. Such acarids are commonly referred to as "dust mites". Two types of allergens are produced by dust mites: Group I allergens, which are released by dust mites via fecal pellets, and Group II allergens which are present in the bodies of the dust mites. It has been determined that the threshold level for dust mite allergen sensitization is about 100–500 mites/gram.

It is known that dust mites derive their nourishment from the dead skin, nail debris, fur, and feathers of humans and animals (often collectively referred to as "squamae"). Mold provides dust mites with vitamins, which helps the dust mites digest squamae. Thus, dust mites live in areas where abundant amounts of squamae can be found, where the temperature is warm, where the humidity is relatively high, and where there is little light (because dust mites are sensitive to solar UV). Consequently, dust mites thrive in substrates that have prolonged contact with humans, e.g., bedding, upholstered furniture, and carpets.

Acaricidal compositions have been developed to treat substrates. Typically, acaricidal compositions include an acaricide and a carrier, such as water or an organic solvent. These acaricidal compositions poison dust mites, but do not reduce environmental conditions that are favorable to dust mites, such as high humidity and abundant food supplies.

Based upon the foregoing, there is a need in the art for a composition for treating substrates to control dust mites, wherein the composition reduces environmental conditions favorable to dust mites. The present invention is directed to such a composition.

SUMMARY OF THE INVENTION

It therefore would be desirable, and is an advantage of the present invention, to provide a composition for treating substrates to control dust mites, wherein the composition reduces environmental conditions favorable to dust mites. In accordance with the present invention, the composition includes a fluoropolymer, a biocidally effective amount of a biocide, and an acaricidally effective amount of an acaricide. Also provided in accordance with the present invention are methods of treating substrates to control dust mites. The methods include the step of applying a composition to the substrate. In one embodiment, the composition includes a fluoropolymer and an acaricidally effective amount of an acaricide. In another embodiment, the composition includes a biocidally effective amount of a biocide, and an acaricidally effective amount of an acaricide.

DETAILED DESCRIPTION OF THE PREFERRED EMBODIMENTS OF THE INVENTION

It should be noted that parts are parts by weight and percents are weight percents unless otherwise indicated or apparent. In addition, when a preferred range such as 5–25 is given, this means preferably at least 5 and preferably not more than 25.

As used herein, the term "acaricide" shall mean a material that kills or materially inhibits the growth, reproduction, or spread of acarids, including but not limited to dust mites. An "acaricidally effective amount" of an acaricide is that amount that will kill or materially inhibit the growth, reproduction or spread of a significant number of acarids.

As used herein, the term "biocide" shall mean a material that kills or materially inhibits the growth, division, reproduction, or spread of microorganisms, such as bacteria, algae, and fungi. A "biocidally effective amount" of a biocide is that amount that will kill or materially inhibit the growth, division, reproduction, or spread of a significant number of microorganisms.

As used herein, the term "fluoropolymer" shall mean any polymer, copolymer, or mixture of polymers, wherein some or all of the hydrogens are replaced with fluorine.

As used herein, the term "powderizing agent" shall mean a material that operates as an inert carrier to render a liquid into a solid.

Preferably, the composition of the present invention is in liquid form and is organic solvent-based. Less preferably, the composition is in liquid form and is water-based. Still less preferably, the composition is in powder form.

The preferred formulation (Formulation 1) for the organic solvent-based embodiment of the composition is as follows:

| | Weight Percent | | |
|---|---|---|---|
| Component | Preferred | Less Preferred | Less Preferred |
| 1. Polymer A | 7.55 | 5–15 | .1–20 |
| 2. Biocide | .25 | .05–1 | .001–5 |
| 3. Acaricide | .1 | .05–3 | .01–10 |
| 4. Solvent A | 92.1 | 81–94.9 | 65–99.88 |

The preferred formulation (Formulation 2) for the water-based embodiment of the composition is as follows:

| | Weight Percent | | |
|---|---|---|---|
| Component | Preferred | Less Preferred | Less Preferred |
| 1. Polymer B | 2.9 | 2–15 | .1–20 |
| 2. Biocide | .25 | .05–1 | .0001–5 |
| 3. Acaricide | .1 | .05–3 | .01–10 |
| 4. Surfactant A | 1.3 | .5–5 | .1–10 |
| 5. Glycol ether A | 2.5 | .5–5 | .1–10 |
| 6. Glycol ether B | 2.5 | .5–5 | .1–10 |
| 7. Water | 90.45 | 66–96.4 | 35–99.5899 |

The preferred formulation (Formulation 3) for the powder embodiment of the composition is as follows:

| | Weight Percent | | |
|---|---|---|---|
| Component | Preferred | Less Preferred | Less Preferred |
| 1. Polymer A | 7.55 | 5–15 | .1–20 |
| 2. Biocide | .25 | .05–1 | .01–2 |
| 3. Acaricide | .1 | .05–3 | .01–10 |
| 4. Powderizing Agent | 92.1 | 81–94.9 | 69–99.88 |

Preferably, polymers A and B prevent water and other polar and non-polar liquids and soils from penetrating the substrate to which the composition of the present invention is applied, and also prevent the biocides A and B and the acaricide from being removed from the substrate by water and other liquids. The polymers A and B preferably reduce the surface energy of the substrate to 16–30 dynes/cm. This low surface energy prevents water and most oils from wetting or spreading over or into the substrate. It is believed that the low surface energy also helps prevent soil, such as squamae, from adhering to the substrate. Thus, the polymers A and B preferably keep the substrate clean and dry, thereby making the substrate less suitable for hosting dust mites.

Preferably, polymer A is a perfluorinated polymer sold under the name Bartex AF NF by TriTex. Bartex AF NF is a mixture comprising 15 weight-percent fluoroalkyl acrylate copolymer solubilized in an 85 weight-percent 1,1-dichloro-1-fluoroethane solvent. Polymer B is preferably a perfluoroalkyl methacrylic copolymer sold under the name Zonyl 8740 by E. I. Du Pont de Nemours. Less preferably, polymers A and B are fluorinated or perfluorinated acrylics, methacrylics, styrenes, or polyethylenes, or other type of fluoropolymers. Still less preferably, polymers A and B are silicone polymers, such as polymethylhydrosiloxane. Still less preferably, polymers A and B are any other polymer, copolymer, or mixture of polymers that provides a water resistant coating.

Preferably, the biocide is active against a broad spectrum of organisms, including Gram negative and Gram positive bacteria, and fungi. It is also preferred if the biocide is not irritating to human skin, is not readily deactivated by soil load, and is compatible with water repellent polymers, such as fluoropolymers. The biocide preferably reduces and prevents the growth of mold, fungi, bacteria, and algae, which are potential food sources for dust mites.

The biocide is preferably didecyldimethylammonium chloride, which is a quaternary ammonium compound sold by Lonza UK Ltd. under the name Bardac 22. Less preferably, the biocide is another quaternary ammonium compound, such as: benzyl trimethyl ammonium chloride, which is sold by Rhodia under the name DMB 451; didecyldimethylammonium chloride, which is sold by the Stepan Company under the name BTC 1010; benzalkonium chloride, which is sold by Bayer AG under the name Zephirol; benzethonium chloride, which is sold by Lonza under the name Hyamine 1622; a dual quaternary ammonium compound, such as a mixture of myristalkonium chloride and quaternium 14, which is sold by the Stepan Company under the name BTC 2125; (BTC 2125 is a mixture comprising 25 weight percent n-alkyl(C12–C18)-n,n-dimethyl-n-benzyl-ammonium chloride (CAS# 68391-01-5), and 25, weight percent alkyldimethylethylbenzyl-ammonium chloride (CAS# 68956-79-6) as active ingredients) or 3-(Trimethoxysilyl)-propyldimethyloctadecyl ammonium chloride. Less preferably the biocide is a mixture of a quaternary ammonium compound with a phenolic compound, wherein the weight ratio of the quaternary ammonium compound to the phenolic compound is from 1:1 to 3:1. Still less preferably, the biocide is a phenolic compound. Phenolic compounds that may be used include ortho-phenylphenol and its sodium salt, which are respectively sold by Dow Chemical under the names Dowicide 1 and Dowicide A; and pentachlorophenol, which is sold by Dow Chemical under the name Dowicide OBCP. Still less preferably, the biocide is an isothiazolin, such as 2-octyl-4-isothiazolin-3-one, which is sold by Rohm and Haas under the name Kathon 893; or 2-bromo-2-nitropropane-1,3-diol, known as bronopol, and sold by the Angus Chemical Company and the Inolex Chemical Company. Still less preferably, the biocide is another known biocide.

Preferably, a biocidally effective amount of the biocide is used in the organic solvent-based composition of the present invention and in the powder-based composition of the present invention. Preferably, a biocidally effective amount of the biocide is also used in the water-based composition of the present invention.

Preferably, the acaricide significantly reduces, and/or prevents an increase in, the number of dust mites present in or on the substrate to which the composition of the present invention is applied. It is also preferred if the acaricide is not irritating to human skin, is compatible with water repellent polymers, such as fluoropolymers, and is effective for an extended period of time, e.g. three years or longer.

Preferably, the acaricide is 3-phenoxybenzyl (1 RS, 3RS)-(1RS, 3SR)-3-(2,2-dichlorovinyl)-2,2-dimethyl-cyclopropanecarboxylate, CAS Registry Number 52645-53-1, which is a synthetic pyrethroid known as permethrin and is sold by McLaughlin Gormley King Company. Less preferably, the acaricide is benzyl benzoate, or another pyrethroid, such as an allethrin, bioresmethrin, cypermethrin, cyhalothrin, deltamethrin, or natural pyrethrum. Still less preferably, the acaricide is another known acaricide.

Preferably, an acaricidally effective amount of the acaricide is used in the organic solvent-based composition of the present invention and in the powder-based composition of the present invention. Preferably, an acaricidally effective amount of the acaricide is used in the water-based composition of the present invention.

The solvent A functions as a carrier in the organic solvent-based composition of the present invention. The solvent A dissolves polymer A, the biocide, and the acaricide and carries them onto the substrate. Once the composition is deposited on the substrate, the solvent A quickly evaporates and leaves no residue behind.

Solvent A is preferably an isoparaffinic solvent sold by the Exxon Chemical Company under the name Isopar G, an organic solvent consisting predominantly C10–C11 isoparaffinic hydrocarbons. Less preferably, solvent A is an alkane, such as hexane, or heptane; kerosene; mineral spirits; an alkyl benzene, such as toluene, or xylene; an ester, such as ethyl acetate; a hydrofluorocarbon, such as 1-H-perfluorohexane; a fluorether; or another known aromatic, halogenated, or aliphatic solvent.

Water functions as a carrier in the water-based composition of the present invention. Surfactant A solubilizes the biocide and the acaricide into the water, while the glycol ether A and the glycol ether B help to solubilize the polymer B into the water. Once the composition is deposited on the substrate, the water evaporates, leaving the surfactant A on the substrate. Without being limited by theory, it is believed that the residual surfactant traps soil onto the substrate and reduces the efficacy of the polymer B. Accordingly, it is important to minimize the amount of surfactant A used in the composition.

Preferably, the surfactant A is a surfactant comprising 2,6,8-trimethyl-4-nonanol with ethylene oxide, which is sold by Union Carbide under the name Tergitol TMN-6. Less preferably, surfactant A is another alcohol alkoxylate, an alkyl phenol alkoxylate, a glucoside, a sorbitan, a block polymer, an amine oxide, an amphoteric surfactant, a quaternary ammonium composition, an anionic surfactant, or a polymeric surfactant. Still less preferably, surfactant A is another known surfactant.

Glycol ether A is preferably dipropylene glycol monomethyl ether, which is sold by Dow Chemical under the name Dowanol DPM. Glycol ether B is preferably dipropylene glycol monobutyl ether, which is sold by Dow Chemical under the name Dowanol DPnB. Less preferably, glycol ethers A and B are other glycol ethers. Still less preferably, the glycol ethers A and B may be replaced with alcohols.

The powderizing agent functions as a carrier in the powder-based composition of the present invention. The powderizing agent renders the polymer A, the biocide, and the acaricide into a solid. Preferably, the powderizing agent is talc, sodium sulfate, sodium carbonate, calcium carbonate, or other carbonate. Less preferably, the powderizing agent is another known powder carrier.

Polymer A, the biocide, the acaricide, and solvent A are blended together using customary and known methods to form the organic solvent-based composition of the present invention. Preferably, the temperature during blending is maintained at ambient temperature, i.e., @ 70° F.

Polymer B, the biocide, the acaricide, surfactant A, glycol ether A, glycol ether B, and the water are blended together using customary and known methods to form the water-based composition of the present invention. Preferably, the temperature during blending is maintained at ambient temperature, i.e., @ 70° F.

Polymer A, the biocide, the acaricide, and the powderizing agent are blended together using customary and known methods to form the powder-based composition of the present invention. Preferably, the temperature during blending is maintained at ambient temperature, i.e., @ 70° F.

Preferably, the organic solvent-based and water-based compositions of the present invention are applied to a substrate using a pump-type sprayer. Less preferably, an aerosol sprayer may be used, which is typically in the form of a steel can. Aerosol propellants, such as isobutane, or $CO_2$, are used in the aerosol sprayer to dispense the organic solvent-based and water-based compositions. Known corrosion inhibitors may also be included to prevent corrosion of the steel can.

The powder-based composition of the present invention may be applied to a substrate from a bottle, box, can, or other container, which is preferably provided with a dispenser, such as a grate, or a plurality of apertures. The powder-based composition is applied by shaking, sprinkling, and/or rubbing the powder composition into the substrate.

The composition of the present invention may be used on any substrate upon which, or within which dust mites may be disposed, or through which dust mites may pass. Such substrates include, but are not limited to, textile fibers (or filaments), fabrics, clothing, carpets, rugs, upholstery, furniture, bedding, mattresses, pillows, curtains, and couches.

The composition of the present invention provides many advantages. When applied to a substrate, the composition kills dust mites that are already present on the substrate, as well as dust mites that later contact the substrate. In addition, the composition keeps the substrate clean and dry, and kills bacteria and fungi, thereby reducing food sources available to dust mites, which helps reduce the population of dust mites already present on the substrate and discourages migration of dust mites to the substrate. In this manner, the composition is both reactive and preventative in terms of controlling dust mites.

The following Examples further illustrate various aspects of the invention. Unless otherwise indicated, the ingredients are combined using methods known in the art or as described above.

EXAMPLE 1

A test was performed to measure the efficacy of the organic solvent-based and water-based compositions of the present invention in controlling *Dermatophagoides farinae* (commonly known as the "American house dust mite") on a carpet substrate.

An organic solvent-based composition was prepared in accordance with Formulation 1 by blending 7.55 parts of Bartex AF NF (perfluorinated polymer), 0.1 parts of Dowicide 1 (orthophenyl phenol), 0.1 parts of permethrin, and 92.25 parts of Isopar G (isoparaffinic solvent). The composition with the foregoing formulation shall be referred to in this Example 1 and in Examples 2 and 3 as the "Solvent Inventive Composition".

A water-based composition was prepared in accordance with Formulation 2 by blending 2.9 parts of Zonyl 8740 (perfluoroalkyl methacrylic copolymer), 0.1 parts of Dowicide A (sodium-orthophenyl phenol), 0.1 parts of permethrin, 1.3 parts of Tergitol TMN-6 (2,6,8-trimethyl-4-nonanol with ethylene oxide), 2.5 parts Dowanol DPM (dipropylene glycol monomethyl ether), 2.5 parts Dowanol DPnB (dipropylene glycol monobutyl ether), and 90.6 parts water. The composition with the foregoing formulation shall be referred to in this Example 1 and in Examples 2 and 3 as the "Aqueous Inventive Composition".

Three sections of carpet were selected. Each section of carpet was the same style and color, and had a size of about 23 inches by 46.5 inches. The sections of carpet were new and not treated with any stain blockers. Using spray bottles, the Solvent Inventive Composition was applied to a first one of the sections, the Aqueous Inventive Composition was applied to a second one of the sections, and a control consisting of water was applied to a third one of the sections. The application rates for each of the compositions was about 20.97 ml per $ft^2$. Following the application of the compositions to the sections, each of the sections was rubbed with a plastic sheet to assure proper coverage. The sections were then allowed to dry for a period of 24 hours.

After drying, the backing of each of the sections was marked with grid lines to make numbered squares that would fit into 15×60 mm petri dishes. Three squares from each of the sections were randomly selected using a random number generator. The carpet squares were then cut from the sections to provide a total of nine squares, three from each section. The three squares from each section constituted a "sample" of the composition applied to the section.

Each square was placed in a petri dish and inoculated with 40 adult American house dust mites. In each square, the mites were innoculated in the center of the square using a fine (000) brush. The petri dishes containing the squares were then covered with paraffin lids and placed in humidity chambers. The petri dishes containing the squares were maintained in the humidity chambers at a relative humidity of about 75% and at room temperature, i.e., about 70–75° F., for 96 hours.

After the 96 hour period, the acute mortality of the American house dust mites in each sample was assessed using a "heat escape procedure", wherein the petri dishes were inverted (with paraffin lids facing down) and placed under a 100 watt light source, such that the heat (@ 108° F.) generated by the light source would drive alive mites to the paraffin lids. The surfaces of the paraffin lids were then examined and the number of alive mites counted. This heat escape procedure was performed a total of three times on each petri dish of the sample, with a new paraffin lid being used for each procedure. The squares in each petri dish were then microscopically examined for mites. Mites were scored as dead if they failed to move one body length in response to gentle brushing. Mortality values were then expressed as mean mortality for the three squares in the sample, ±standard error margin (SEM).

A t-test of proportions was performed to compare mortality between the samples of the Solvent Inventive Composition, the Aqueous Inventive Composition, and the negative control. When the mortality of the house dust mites in the samples of the Solvent Inventive composition, the Aqueous Inventive Composition, and the negative control were compared by the studentized t-test of proportions ($P<0.05$), it was shown that the Solvent Inventive Composition and the Aqueous Inventive Composition provided significantly different results from the negative control and each other. The results of the test were as follows:

|  | Mortality, % |
|---|---|
| Solvent-Based Inventive Composition | 100 ± 0.0 |
| Water-Based Inventive Composition | 72.5 ± 5.2 |
| Negative Control | 10.8 ± 0.8 |

As shown by the above results, the Solvent Inventive Composition and the Aqueous Inventive Composition both provide effective control of dust mites. The Solvent Inventive Composition provides especially good dust mite control, having killed all of the dust mites in the sample, which was a surprising and unexpected result.

EXAMPLE 2

A water repellency test was performed to measure the efficacy of the organic solvent-based and water-based compositions of the present invention in repelling water. The test was performed in accordance with a modified version of the American Association of Textile Chemists and Colorists (AATCC) Test Method 22-1989 Water Repellency; Spray Test. Water repellency is defined by the AATCC as the characteristic of a fibre, yarn, or fabric to resist wetting.

The Solvent Inventive Composition was applied to a piece of untreated cotton fabric, and the Aqueous Inventive Composition was applied to another piece of cotton fabric. Water was poured over the pieces of cotton fabric, and their repellency was then evaluated. No sticking or wetting of the upper surfaces of the pieces of cotton fabric was observed.

As shown by the above results, the application of the Solvent Inventive Composition and the Aqueous Inventive Composition to substrates renders the substrates water repellant.

EXAMPLE 3

An oil repellency test was performed to measure the efficacy of the organic solvent-based and water-based compositions of the present invention in repelling oil. The test was performed in accordance with AATCC Test Method 118-1992 Oil Repellency; Hydrocarbon Test. The test utilizes standard test liquids consisting of a series of hydrocarbons with varying surface tensions.

The Solvent Inventive Composition was applied to a piece of cotton fabric, and the Aqueous Inventive Composition was applied to another piece of cotton fabric. Drops of the test liquids were applied to each piece of cotton fabric. After each drop of test liquid was applied to a piece of cotton fabric, the piece of cotton fabric was observed for wetting, wicking, and contact angle. The piece of cotton fabric was then given a grade number, which was the highest number test liquid that did not wet the piece of cotton fabric. Grade 0 is the lowest oil repellency, while grade 8 is the highest oil repellency.

The piece of cotton fabric to which the Solvent Inventive Composition was applied was given a grade number of 6, while the piece of cotton fabric to which the Aqueous Inventive Composition was applied was given a grade number of 2. Grade 6 corresponds to n-decane, while grade 2 corresponds to a mixture of 65 volume percent of liquid paraffin and 35 volume percent of n-hexadecane.

As shown by the above results, the application of the Solvent Inventive Composition to a substrate will cause the substrate to repel most oils. The application of the Aqueous Inventive Composition to a substrate will cause the substrate to repel some oils.

EXAMPLE 4

A test was performed to measure the efficacy of the organic solvent-based composition of the present invention in controlling bacteria.

A plurality of organic solvent-based compositions, S1–S7, were prepared in accordance with Formulation 1 by blending 7.55 parts of Bartex AF NF (perfluorinated polymer), 0.1 parts of permethrin, 0.1 parts Dowicide 1 (ortho-phenylphenol), and varying amounts of Bardac 22 (didecyldimethylammonium chloride) and Isopar G (isoparaffinic solvent). The varying weight percents of Bardac 22 and Isopar G for the compositions were as follows:

| Composition | Bardac 22 | Isopar G |
|---|---|---|
| S1 | 0.0 | 92.25 |
| S2 | 0.009 | 92.241 |
| S3 | 0.019 | 92.231 |
| S4 | 0.038 | 92.212 |
| S5 | 0.075 | 92.175 |
| S6 | 0.15 | 92.10 |
| S7 | 0.3 | 91.95 |

A 0.5 $m^2$ sample of untreated, cotton-based upholstery fabric was cut into a plurality of 20 mm×20 mm samples. Thirty-five samples were used in the test, a set of five samples being used for each composition. Each set of samples was immersed in its respective composition for approximately 5 minutes. The sets of samples were then removed and allowed to drain on an inclined surface. The sets of samples were then transferred to sterile petri dishes and allowed to stand overnight in a fume extraction cabinet to dry thoroughly.

Three samples from each set were selected at random and placed onto the surface of a Malt Extract Agar plate. Thus, seven plates, with three samples in each plate were used, one plate being used for each composition. Each of the plates was then inoculated with an aliquot (100 μl spread uniformly over both the plate and the samples) of a spore suspension of *Penicillium pinophylum* (IMI 114933: ca $10^7$ spores per ml). The plates were then incubated at 24° C. for 5 days. The plates were then inspected for growth, with the following results:

| Comp. | Growth |
|---|---|
| S1 | samples virtually overgrown |
| S2 | samples partially overgrown |
| S3 | some surface growth on samples |
| S4 | surface growth restricted to edges of samples |
| S5 | little surface growth, slight zone of inhibition |
| S6 | no surface growth, moderate zone of inhibition |
| S7 | no surface growth, significant zone of inhibition |

As shown by the above results, the organic solvent-based composition of the present invention has good biocidal properties, which helps reduce food sources available to dust mites.

While the invention has been shown and described with respect to particular compositions thereof, those compositions are for the purpose of illustration rather than limitation, and other variations and modifications of the specific compositions herein described will be apparent to those skilled in the art, all within the intended spirit and scope of the invention. Accordingly, the invention is not to be limited in scope and effect to the specific compositions herein described, nor in any other way that is inconsistent with the extent to which the progress in the art has been advanced by the invention.

What is claimed is:

1. A composition for treating a substrate upon which dust mites live or through which dust mites pass, said composition comprising a mixture of:
    1) a fluoropolymer which, upon application to said substrate, reduces the surface energy of said substrate to 16 to 30 dynes/cm;
    2) an effective amount of a biocide which inhibits the growth of mold, fungi, bacteria and algae in or on said substrate which are potential food sources for said dust mites;
    3) an effective amount of an acaricide which reduces or prevents an increase in the number of dust mites present in or on said substrate.

2. The composition of claim 1, wherein the acaracide is a synthetic pyrethroid.

3. The composition of claim 2, wherein the acaracide is permethrin, and the biocide is didecyldimethylammonium chloride.

4. The composition of claim 3, wherein the flouropolymer is perfluorinated.

5. The composition of claim 2, further comprising an organic solvent.

6. The composition of claim 2, wherein the biocide is a quaternary ammonium compound.

7. The composition of claim 6, further comprising 65 to 99.88 weight percent isoparrafinic solvent, and wherein the fluoropolymer comprises from 0.1 to 20 weight percent of the composition.

8. The composition of claim 2, further comprising 66 to 96.4 weight percent water, 0.5 to 5 weight percent surfactant, and 1 to 10 weight percent glycol ether.

9. The composition of claim 8, wherein the biocide is a quaternary ammonium compound.

10. The composition of claim 2, wherein said composition comprises 0.1 to 20 weight percent fluoropolymer, 0.001 to 5 weight percent of a quaternary ammonium compound, and 0.01 to 10 weight percent of a synthetic pyrethroid.

11. The composition of claim 10, wherein the fluoropolymer is a perfluorinated polymer.

12. The composition of claim 11, wherein the quaternary ammonium compound is didecyldimethylammonium chloride.

13. The composition of claim 12, wherein the pyrethroid is permethrin.

14. The composition of claim 2, wherein the fluoropolymer is a perfluoroalkyl methacrylic (co)polymer.

15. The composition of claim 2, wherein said biocide prevents the growth of fungi.

16. The composition of claim 2, wherein said composition comprises 0.001 to 5 weight percent biocide.

17. The composition of claim 2, wherein said fluoropolymer is perfluorinated.

18. The composition of claim 2, comprising 0.1 to 20 weight percent fluoropolymer.

19. The composition of claim 2, wherein said composition consists essentially of said fluoropolymer, biocide and acaracide.

20. The composition of claim 2, further comprising about 65 to 99.8 weight percent organic solvent.

21. A method of treating a substrate to control dust mites, said method comprising the step of applying to a substrate upon which dust mites live or through which dust mites pass a composition comprising a mixture of:
    1) a fluoropolymer which, upon application to said substrate, reduces the surface energy of said substrate to 16 to 30 dynes/cm;
    2) an effective amount of a biocide which inhibits the growth of mold, fungi, bacteria and algae in or on said substrate which are potential food sources for said dust mites;
    3) an effective amount of an acaricide which reduces or prevents an increase in the number of dust mites present in or on said substrate.

22. The method of claim 21, wherein the acaracide is a synthetic pyrethroid.

23. The method of claim 22, wherein said composition further comprises 65 to 99.88 weight percent organic solvent.

24. The method of claim 22, wherein said composition consists essentially of said fluoropolymer, biocide and acaracide.

25. The method of claim 22, wherein said composition is in liquid form.

26. The method of claim 22, wherein the acaracide is permethrin, and the biocide is didecyldimethylammonium chloride.

27. The method of claim 22, wherein the fluoropolymer is perfluorinated.

28. The method of claim 22, wherein the biocide is a quaternary ammonium compound.

29. The method of claim 22, wherein the composition further comprises 66 to 96.4 weight percent water, 0.5 to 5 weight percent surfactant, and 1 to 10 weight percent glycol ether.

30. The method of claim 22, wherein the fluoropolymer is a perfluoroalkyl methacrylic (co)polymer.

31. The method of claim 22, wherein said composition comprises 0.001 to 5 weight percent biocide.

* * * * *

UNITED STATES PATENT AND TRADEMARK OFFICE
CERTIFICATE OF CORRECTION

PATENT NO. : 6,379,686 B1
DATED : April 30, 2002
INVENTOR(S) : Harris et al.

It is certified that error appears in the above-identified patent and that said Letters Patent is hereby corrected as shown below:

Column 3,
Line 62, please delete "amixture" and insert therefor -- a mixture --.

Column 8,
Line 58, please delete "20 mmx20 mm" and insert therefor -- 20mm x 20mm --.

Column 9,
Line 43, please delete "30 dyncs/cm" and insert therefor -- 30 dynes/cm --.

Signed and Sealed this

Eleventh Day of February, 2003

JAMES E. ROGAN
*Director of the United States Patent and Trademark Office*